(12) United States Patent
Arnon

(10) Patent No.: US 7,292,719 B2
(45) Date of Patent: Nov. 6, 2007

(54) SYSTEM AND METHOD FOR IMAGING

(75) Inventor: Boaz Arnon, Lod (IL)

(73) Assignee: Real Imaging Ltd., Lod (IL)

( * ) Notice: Subject to any disclaimer, the term of this patent is extended or adjusted under 35 U.S.C. 154(b) by 0 days.

(21) Appl. No.: 11/649,290

(22) Filed: Jan. 4, 2007

(65) Prior Publication Data

US 2007/0110293 A1    May 17, 2007

Related U.S. Application Data

(63) Continuation-in-part of application No. PCT/IL2005/000707, filed on Jul. 4, 2005.

(60) Provisional application No. 60/586,162, filed on Jul. 7, 2004.

(51) Int. Cl.
*G06K 9/00* (2006.01)

(52) U.S. Cl. .................. 382/128; 128/922; 382/285; 382/294; 250/316.1; 702/135

(58) Field of Classification Search ................ 382/100, 382/128, 130, 131, 132, 154, 278, 284, 294, 382/302; 128/922; 702/135; 374/100; 250/316.1, 250/330
See application file for complete search history.

(56) References Cited

U.S. PATENT DOCUMENTS

| | | | | |
|---|---|---|---|---|
| 5,492,122 A | * | 2/1996 | Button et al. ............... | 600/411 |
| 5,517,602 A | * | 5/1996 | Natarajan .................... | 345/419 |
| 6,023,637 A | * | 2/2000 | Liu et al. ..................... | 600/474 |
| 6,438,255 B1 | * | 8/2002 | Lesniak ....................... | 382/107 |
| 6,442,419 B1 | * | 8/2002 | Chu et al. .................... | 600/474 |
| 6,500,121 B1 | * | 12/2002 | Slayton et al. .............. | 600/439 |
| 7,072,504 B2 | * | 7/2006 | Miyano et al. .............. | 382/154 |
| 7,157,714 B2 | * | 1/2007 | Del Grande ............. | 250/341.6 |
| 2001/0046316 A1 | * | 11/2001 | Miyano et al. .............. | 382/154 |
| 2005/0065429 A1 | * | 3/2005 | Zhou .......................... | 600/412 |
| 2006/0062448 A1 | * | 3/2006 | Hirsch et al. ................ | 382/154 |

\* cited by examiner

*Primary Examiner*—Vikkram Bali
*Assistant Examiner*—Anand Bhatnagar

(57) ABSTRACT

A system for determining presence or absence of one or more thermally distinguishable objects in a living body is disclosed. The system comprises a combined image generator configured for combining non-thermographic three-dimensional data of a three-dimensional tissue region in the living body with thermographic two-dimensional data of the tissue region so as to generate three-dimensional temperature data associated with the three-dimensional tissue region. In a preferred embodiment the combined image generator comprises a computing device configured for calculating the location and/or orientation of the thermally distinguishable object in the three-dimensional tissue region, based on the three-dimensional temperature data.

41 Claims, 16 Drawing Sheets

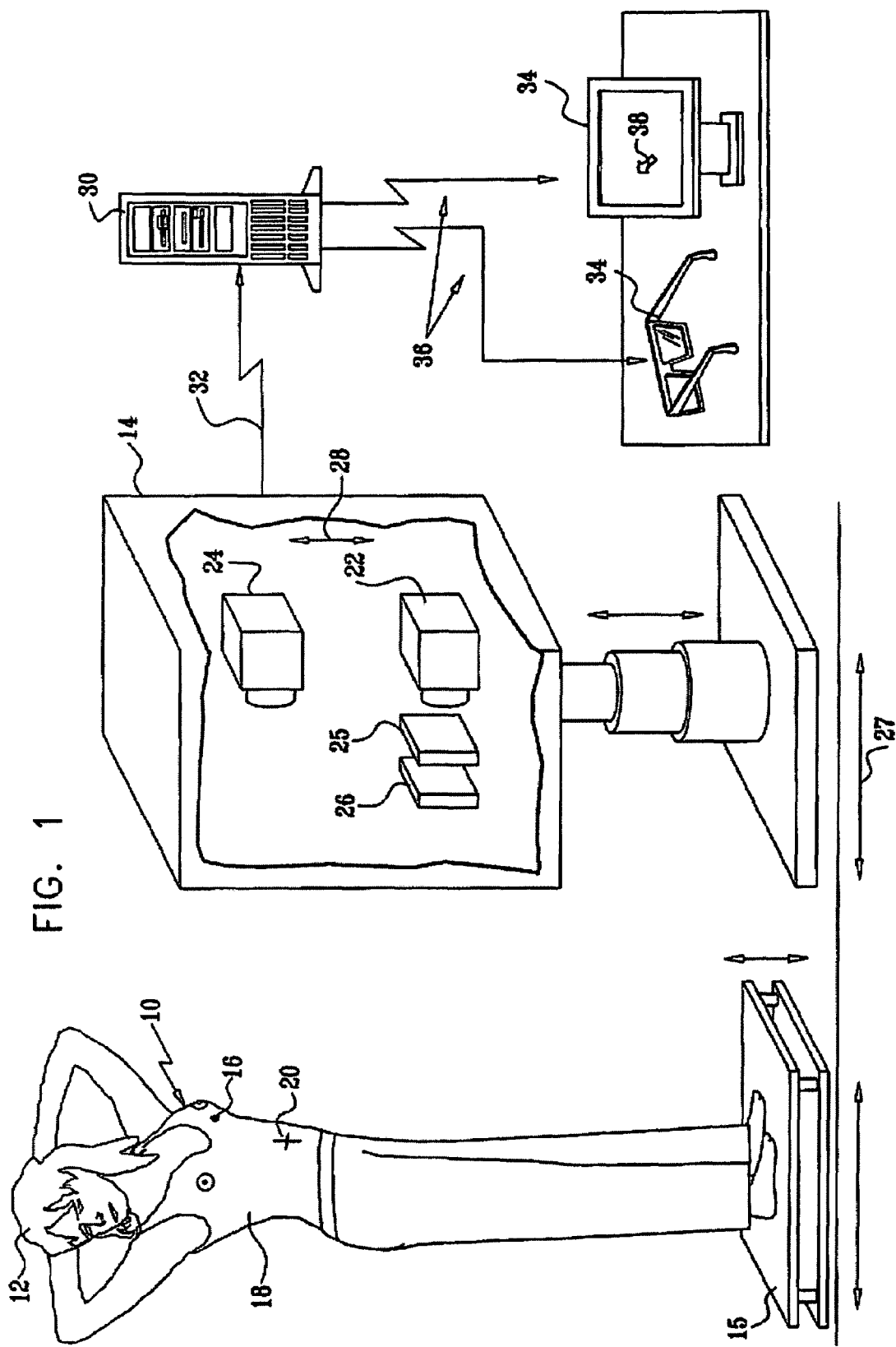

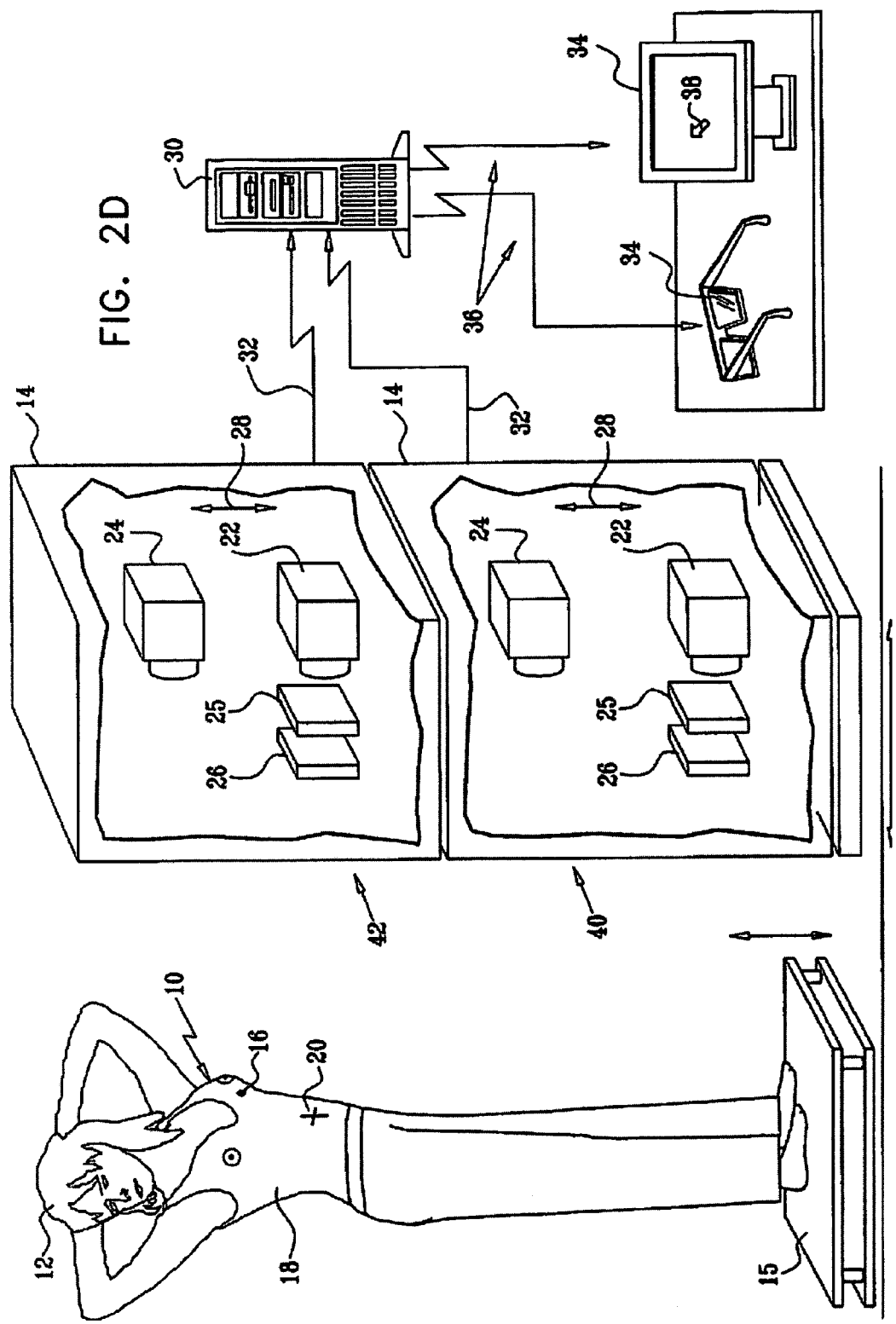

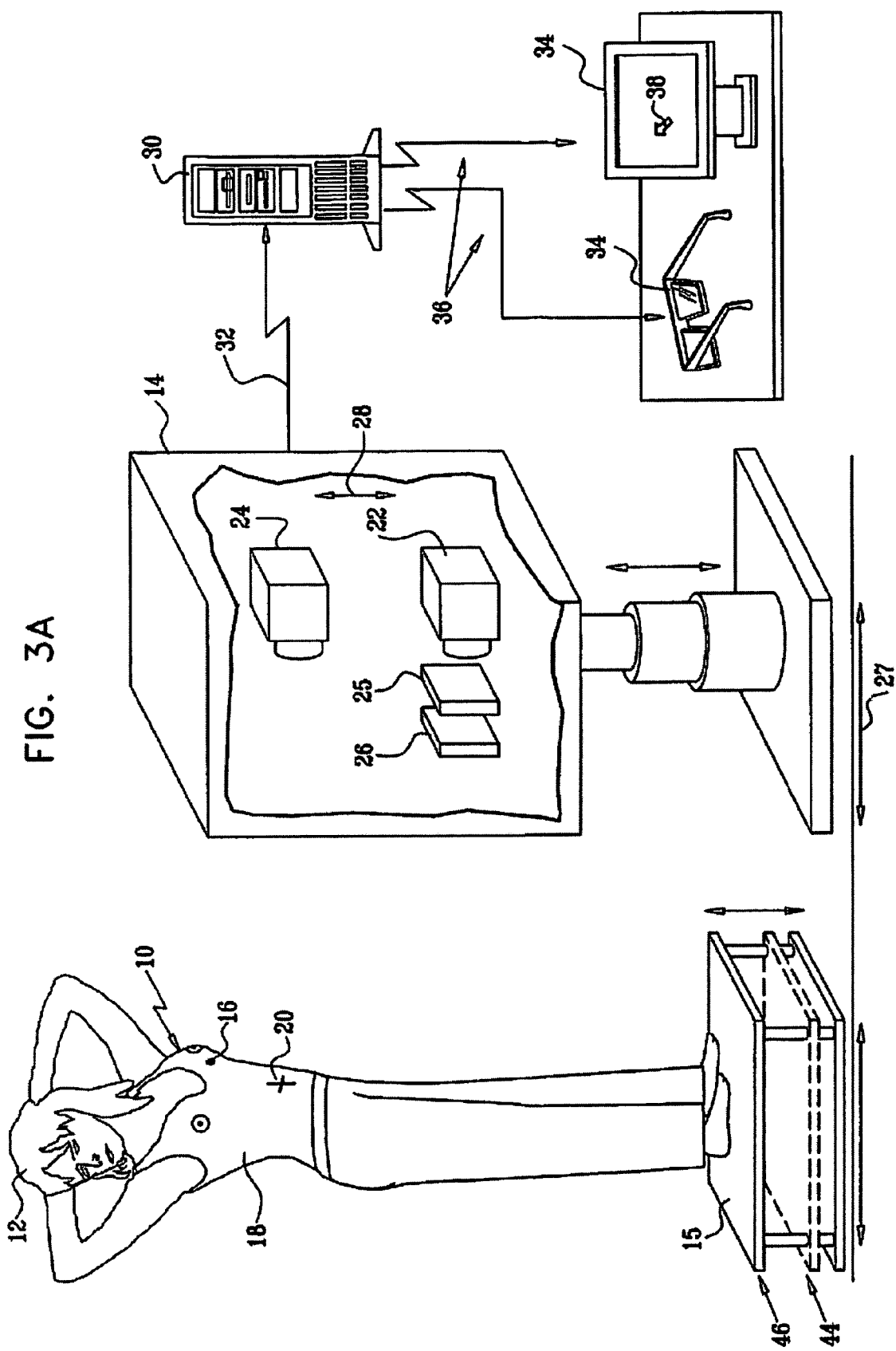

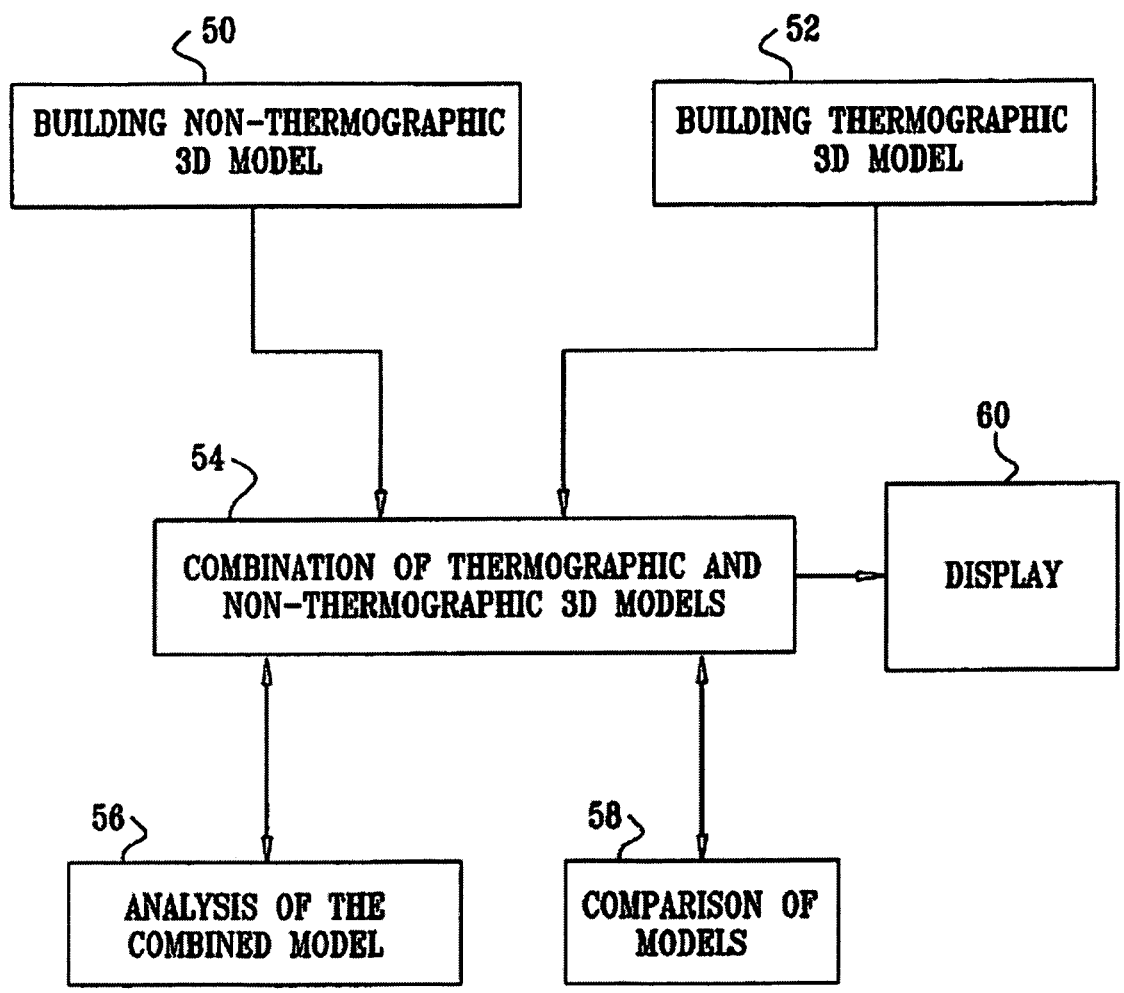

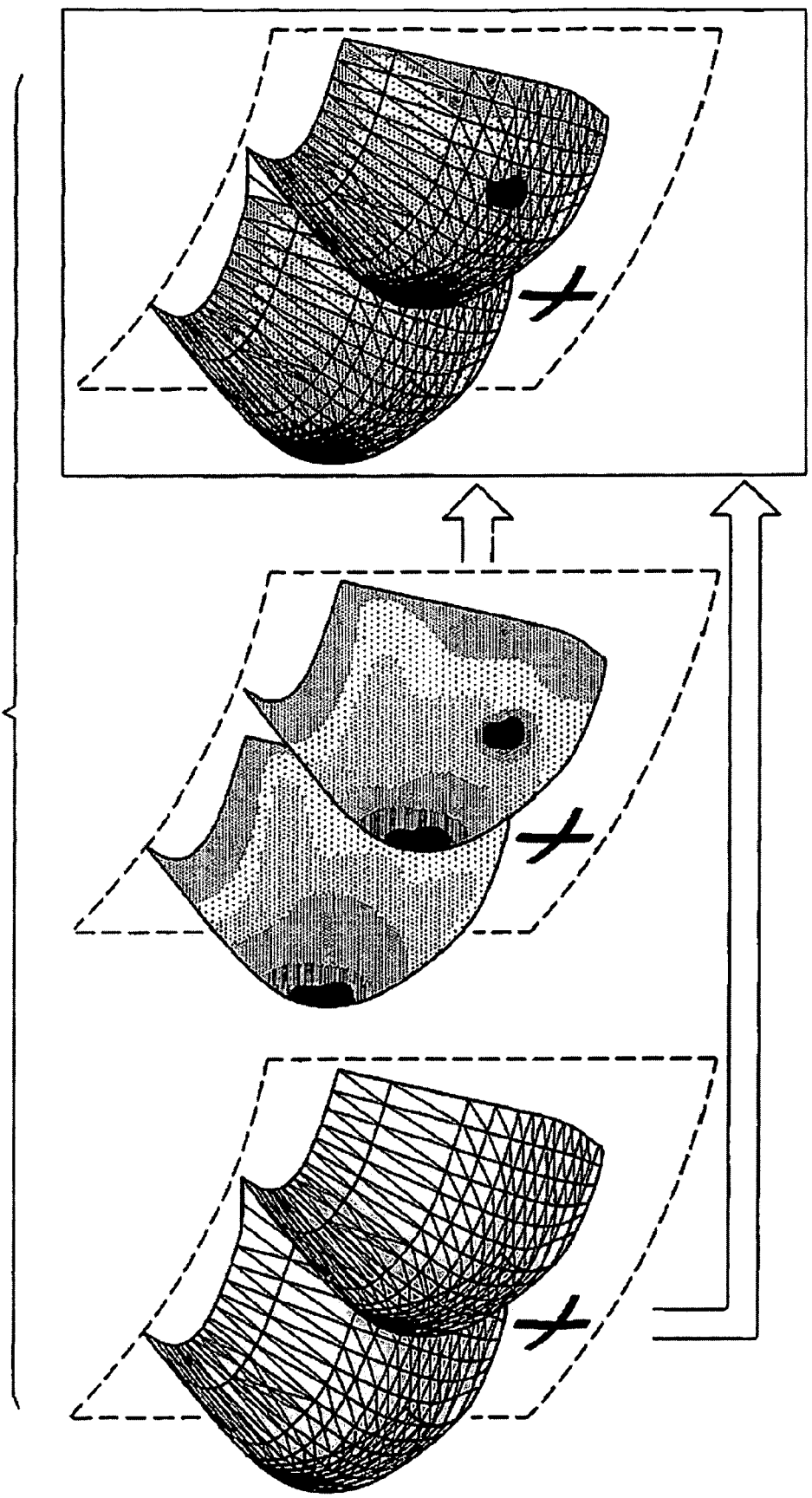

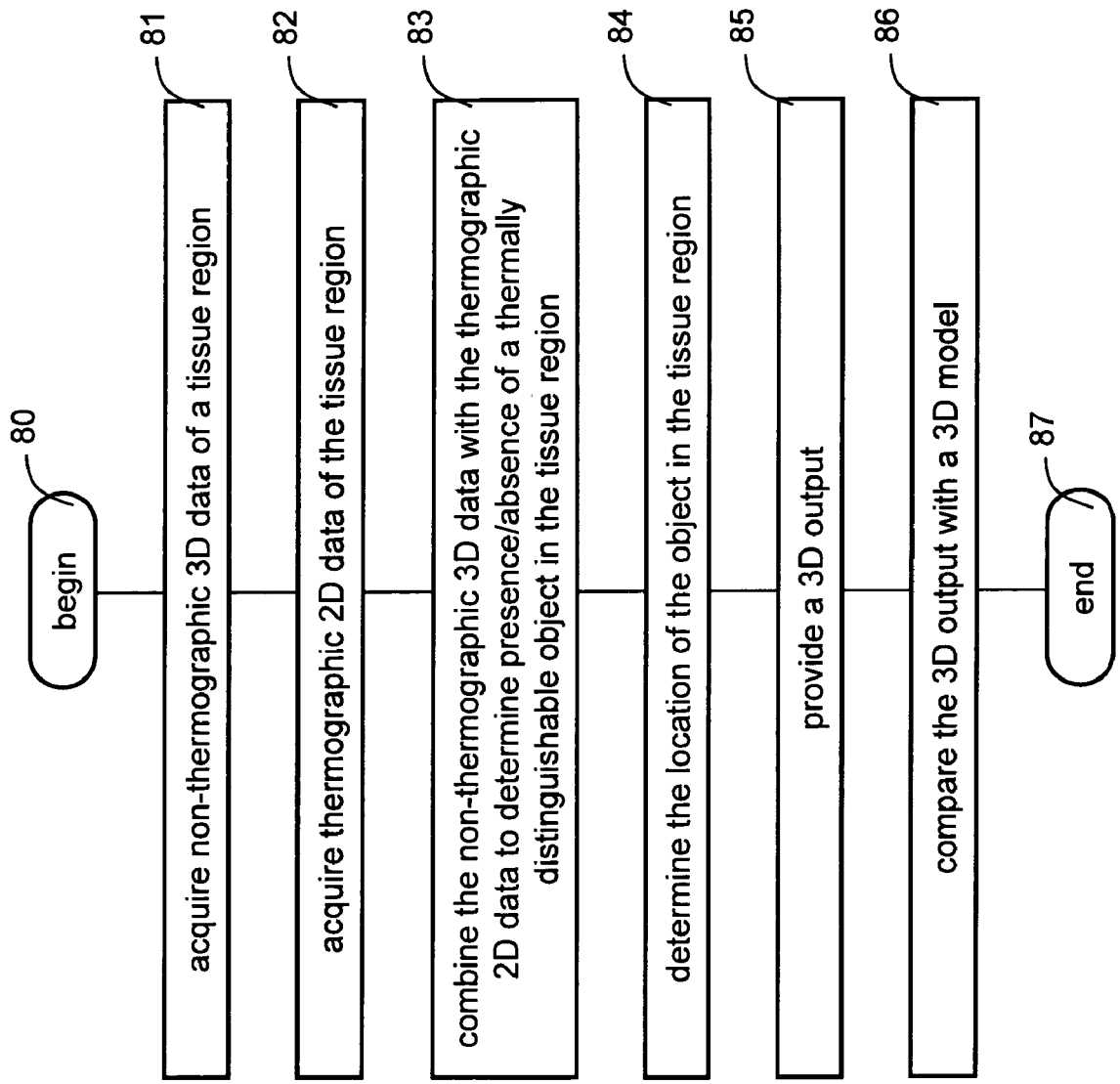

SYSTEM AND METHOD FOR IMAGING

RELATED APPLICATIONS

This application is a continuation-in-part of PCT Patent Application No. PCT/IL2005/000707, filed on Jul. 4, 2005, which claims the benefit of U.S. Provisional Patent Application No. 60/586,162, filed on Jul. 7, 2004, the contents of which are hereby incorporated by reference.

FIELD AND BACKGROUND OF THE INVENTION

The present invention relates to imaging, and, more particularly, to a system and method for determining presence, absence and/or location of a thermally distinguishable tissue region in a living body.

A viewer of a two-dimensional image perceives a structure such as depth, thickness or the like, when the two-eyes of the viewer see slightly different images of a three-dimensional scene. The brain of the viewer transforms the different images viewed by the left eye and right eye into information relating to the third dimension of the image, and the image appears to be "three-dimensional". A technique in which such structures are visually understood is known as stereoscopy.

In a conventional imaging apparatus, a visible stereoscopic image is formed using a left camera which images the scene from the left of the scene, a right camera which images the scene from the right of the scene, and a three-dimensional image synthesis device which synthesizes images obtained by the left and right cameras.

In medical applications, oftentimes an infrared camera is employed, for example, for diagnosing a thermally distinguishable site a human body or for other purposes. Infrared cameras produce a two-dimensional image known as a thermographic image. The thermographic image is typically obtained by receiving from the body of the subject radiation at any one of several infrared wavelength ranges, and analyzing the radiation to provide a two-dimensional temperature map of the surface. The thermographic image can be in the form of either or both of a visual image and corresponding temperature data. The output from infrared cameras used for infrared thermography typically provides an image comprising a plurality of pixel data points, each pixel providing temperature information which is visually displayed, using a color code or grayscale code. The temperature information can be further processed by computer software to generate for example, mean temperature for the image, or a discrete area of the image, by averaging temperature data associated with all the pixels or a sub-collection thereof.

Based on the thermographic image, a physician diagnoses the site, and determines, for example, whether or not the site includes an inflammation. It is recognized that the use of an infrared camera has a problem in that the obtained image is not as realistic as an actual visual observation, and thus sufficient information required for diagnosis is not obtained. Accordingly, the diagnosis of a subtle inflammation symptom relies heavily on the experience and intuition of the physician.

A technique attempting to resolve the above drawback is disclosed in U.S. Pat. No. 7,072,504. In this technique, two infrared cameras (left and right) are used in combination with two visible light cameras (left and right). The infrared cameras are used to provide a three-dimensional thermographic image and the visible light cameras are used to provide a three-dimensional visible light image. The three-dimensional thermographic and three-dimensional visible light images are displayed to the user in an overlapping manner.

Also of interest is U.S. Pat. No. 6,442,419 disclosing a scanning system including an infrared detecting mechanism which performs a 360° data extraction from an object, and a signal decoding mechanism, which receives electrical signal from the infrared detecting mechanism and integrates the signal into data of a three-dimensional profile curved surface and a corresponding temperature distribution of the object.

The above solutions, however, are far from being satisfactory, particularly in the field of medical imaging, because they fail to provide sufficient resolution for the physician to accurately determine the location of a thermally distinguishable tissue region in the body of the subject.

The present invention provides solutions to the problems associated with prior art thermographic imaging techniques.

SUMMARY OF THE INVENTION

The present invention seeks to provide a system and method for combination of three-dimensional non-thermographic data with two-dimensional thermographic data, preferably for medical diagnostic purposes.

Thus, according to one aspect of the present invention there is provided a system for determining presence or absence of one or more thermally distinguishable objects in a living body, e.g., human body. The system comprises a combined image generator configured for combining non-thermographic three-dimensional data of a three-dimensional tissue region in the living body with thermographic two-dimensional data of the tissue region so as to generate three-dimensional temperature data associated with the three-dimensional tissue region.

According to further features in preferred embodiments of the invention described below, the system further comprises non-thermographic image data acquisition functionality configured for acquiring the non-thermographic three-dimensional data.

According to still further features in the described preferred embodiments the system further comprises thermographic image data acquisition functionality configured for acquiring the thermographic two-dimensional data.

According to still further features in the described preferred embodiments the system further comprises a housing containing the non-thermographic image data acquisition functionality and the thermographic image data acquisition functionality.

According to still further features in the described preferred embodiments the system further comprises a positioning device operative to reposition the housing.

According to still further features in the described preferred embodiments the combined image generator comprises a computing device configured for calculating the location of the thermally distinguishable object in the three-dimensional tissue region, based on the three-dimensional temperature data.

According to still further features in the described preferred embodiments the system further comprises a display. The computing device is preferably in communication with the display and is configured for transmitting a visibly sensible three-dimensional output indicating the location to the display.

According to still further features in the described preferred embodiments the system further comprises a communication network configured for establishing the communication between the computing device and the display.

According to still further features in the described preferred embodiments the system further comprises a comparing functionality configured for comparing the three-dimensional temperature data to at least one three-dimensional model.

According to still further features in the described preferred embodiments the computing device is configured for computing a non-thermographic three-dimensional model, and computing spatial data of the non-thermographic three-dimensional model so as to generate spatial data pertaining to the location and/or orientation of the thermally distinguishable object within the living body.

According to still further features in the described preferred embodiments the computing device is configured for computing spatial temperature data of the non-thermographic three-dimensional model.

According to still further features in the described preferred embodiments the display is operative to display a pointer.

According to still further features in the described preferred embodiments the system further comprises a positioning device operative to reposition the non-thermographic image data acquisition functionality or the thermographic image data acquisition functionality.

According to still further features in the described preferred embodiments the communications network is configured for establishing the communication between at least two of the non-thermographic image data acquisition functionality, the thermographic image data acquisition functionality and the combined image generator.

According to still further features in the described preferred embodiments the system further comprises a positioning device operative to reposition the living body.

According to another aspect of the present invention there is provided a method of determining presence or absence of a thermally distinguishable object in a living body. The method comprises combining non-thermographic three-dimensional data of a three-dimensional tissue region in the living body with thermographic two-dimensional data of the tissue region so as to generate three-dimensional temperature data associated with the three-dimensional tissue region, thereby determining the presence or absence of the thermally distinguishable object.

According to further features in preferred embodiments of the invention described below, the method further comprises using the three-dimensional temperature data for determining the location of the thermally distinguishable object in the three-dimensional tissue region.

According to still further features in the described preferred embodiments the method further comprises providing a visibly sensible three-dimensional output indicating the location.

According to still further features in the described preferred embodiments the method further comprises comparing the three-dimensional temperature data to at least one three-dimensional model.

According to still further features in the described preferred embodiments the non-thermographic three-dimensional data are obtained by combining a plurality of two-dimensional images.

According to still further features in the described preferred embodiments the non-thermographic three-dimensional data comprise a three-dimensional image acquired using a visible light camera.

According to still further features in the described preferred embodiments the method further comprises acquiring the non-thermographic three-dimensional data using at least one non-thermographic image data acquisition functionality.

According to still further features in the described preferred embodiments the acquiring of the non-thermographic three-dimensional data comprises a plurality of sequential data acquisition steps, and the method further comprises repositioning at least one of the data acquisition functionality and the living body between successive data acquisition steps.

According to still further features in the described preferred embodiments the plurality of sequential data acquisition steps comprises a first two-dimensional data acquisition step performed at a first perspective view and a second two-dimensional data acquisition step performed as a second perspective view, and the method further comprises combining two-dimensional data from the first step and the second step so as to form the non-thermographic three-dimensional data.

According to still further features in the described preferred embodiments the acquiring of non-thermographic three-dimensional data comprises simultaneously acquiring non-thermographic two-dimensional datasets from a plurality of perspective viewpoints with respect to the surface of the three-dimensional tissue region. According to still further features in the described preferred embodiments and the method further comprises combining the two-dimensional datasets so as to form the non-thermographic three-dimensional data.

According to still further features in the described preferred embodiments the method further comprises acquiring the thermographic two-dimensional data, using at least one thermographic image data acquisition functionality.

According to still further features in the described preferred embodiments the acquiring of the thermographic two-dimensional data comprises a plurality of sequential data acquisition steps, and the method further comprises repositioning at least one of the data acquisition functionality and the living body between successive data acquisition steps.

According to still further features in the described preferred embodiments the combining is performed such that data acquired at each thermographic two-dimensional data acquisition step is combined with the non-thermographic three-dimensional data.

According to still further features in the described preferred embodiments the acquiring of thermographic two-dimensional data comprises simultaneously acquiring thermographic two-dimensional datasets from a plurality of perspective viewpoints with respect to the surface of the three-dimensional tissue region. According to still further features in the described preferred embodiments and the method further comprises combining each thermographic two-dimensional dataset with the non-thermographic three-dimensional data.

According to still further features in the described preferred embodiments the combining comprises computing a non-thermographic three-dimensional model, and computing spatial data of the non-thermographic three-dimensional model so as to generate spatial data pertaining to the location and/or orientation of the thermally distinguishable object within the living body.

According to still further features in the described preferred embodiments the combining comprises computing spatial temperature data of the non-thermographic three-dimensional model.

According to still further features in the described preferred embodiments the thermally distinguishable object comprises a tumor.

According to still further features in the described preferred embodiments the tumor comprises a cancerous tumor.

In various exemplary embodiments of the invention the system includes the non-thermographic image data acquisition functionality, the thermographic image data acquisition functionality and the combined image generator which provides a visually sensible three-dimensional output indicating the location and orientation of the object within the at least a portion of the body.

In accordance with another preferred embodiment of the present invention the non-thermographic image data and the thermographic image data include at least one three-dimensional image.

In accordance with yet another preferred embodiment of the present invention the non-thermographic image data acquisition functionality includes a stills camera or a digital camera.

According to still further features in the described preferred embodiments the non-thermographic image data acquisition functionality comprises a plurality of cameras configured and positioned for acquiring a plurality of non-thermographic two-dimensional datasets from a plurality of perspective viewpoints with respect to the surface of the three-dimensional tissue region. According to still further features in the described preferred embodiments the non-thermographic image data acquisition functionality comprises a combiner configured for combining the plurality of non-thermographic two-dimensional datasets so as to form the non-thermographic three-dimensional data.

Optionally and preferably, the stills camera includes a black-and-white stills camera or a color stills camera. Additionally or alternatively, the digital camera includes CCD or CMOS. In accordance with a further preferred embodiment of the present invention the non-thermographic image data acquisition functionality also includes a polarizer. Alternatively, the non-thermographic image data acquisition functionality may also include a color filter.

According to still further features in the described preferred embodiments the thermographic image data acquisition functionality is sensitive to infra-red wavelengths. According to still further features in the described preferred embodiments the thermographic image data acquisition functionality comprises a plurality of infrared cameras configured and positioned for acquiring a plurality of thermographic two-dimensional datasets from a plurality of perspective viewpoints with respect to the surface of the three-dimensional tissue region. According to still further features in the described preferred embodiments the combined image generator is configured for combining the non-thermographic three-dimensional data with each thermographic two-dimensional dataset.

According to still further features in the described preferred embodiments the computing device includes a PC or a PDA and the display includes of at least one LCD, at least one CRT or a plasma screen. As a further alternative, the display may include two LCDs or two CRTs packaged together in an eyeglasses structure. Preferably, the display is operative to display a pointer.

In accordance with another preferred embodiment of the present invention the communications networks include at least one of intranet, Internet, Blue-Tooth communications network, cellular communications network, infra-red communications network and radio frequency communications network.

In various exemplary embodiments of the invention the method comprises acquiring the non-thermographic image data, acquiring the thermographic image data, and combining the non-thermographic and thermographic image data to provide a visually sensible three-dimensional output indicating the location and orientation of the object within the living body.

In accordance with another preferred embodiment of the present invention the acquiring of the non-thermographic image data includes acquiring first non-thermographic image data in a first relative position of the body and at least one non-thermographic image data acquisition functionality and acquiring at least second non-thermograpic image data in at least a second relative position of the body and at least one non-thermographic image data acquisition functionality.

In accordance with yet another preferred embodiment of the present invention the acquiring thermographic image data includes acquiring first thermographic image data in a first relative position of the body and at least one thermographic image data acquisition functionality and acquiring at least second thermographic image data in at least a second relative position of the body and at least one thermographic image data acquisition functionality.

In accordance with a further preferred embodiment of the present invention the at least second relative position is configured by repositioning the body. Alternatively, the at least second relative position is configured by repositioning the at least one non-thermographic image data acquisition functionality or the at least one thermographic image data acquisition functionality. As a further alternative, the first relative position is configured by a first the non-thermographic image data acquisition functionality or by a first thermographic image data acquisition functionality and the at least second relative position is configured by at least a second the non-thermographic image data acquisition functionality or by at least a second thermographic image data acquisition functionality.

In accordance with another further preferred embodiment of the present invention the second relative position is configured by repositioning the housing. Alternatively, the first relative position is configured by a first the non-thermograpic image data acquisition functionality or a first thermographic image data acquisition functionality enclosed within a first housing, and the at least second relative position is configured by at least a second the non-thermograpic image data acquisition functionality or at least a second thermographic image data acquisition functionality enclosed within at least a second housing.

Also contemplated is a computation of: (i) a non-thermographic three-dimensional model of the non-thermographic image data, and (ii) a thermographic three-dimensional model of the thermographic image data. In this embodiment, the non-thermographic three-dimensional model and the thermographic three-dimensional model are combined to provide the visually sensible three-dimensional output.

In accordance with a still further preferred embodiment of the present invention the computation of a non-thermographic three-dimensional model of the non-thermographic image data also includes computing spatial data of the non-thermographic three-dimensional model. Preferably, the computing spatial data of the non-thermographic three-dimensional model includes computing the X, Y and Z coordinates of the portion of the human body. Additionally or alternatively, the computing a non-thermographic three-dimensional model of the non-thermographic image data also includes obtaining information relating to the color, hue or tissue texture of the portion of the human body.

In accordance with another preferred embodiment of the present invention the computation of a thermographic three-dimensional model of the non-thermographic image data also includes computing spatial temperature data of the non-thermographic three-dimensional model. Preferably, the computing spatial data of the non-thermographic three-dimensional model includes computing the temperature of the portion of the human body along the X, Y and Z coordinates.

In accordance with yet another preferred embodiment of the present invention the combination includes substantially positioning the non-thermographic three-dimensional model and the thermographic three-dimensional model in parallel manner. Preferably, this is achieved by substantially positioning a marker. Additionally or alternatively this can be achieved by substantially positioning X, Y and Z coordinates of the non-thermographic three-dimensional model and the thermographic three-dimensional model.

In accordance with still another preferred embodiment of the present invention the displaying the visually sensible three-dimensional output also includes displaying a pointer. Additionally or alternatively the displaying the visually sensible three-dimensional output also includes displaying sectional views of the visually sensible three-dimensional output.

In accordance with a further preferred embodiment of the present invention the method also includes extracting information from the visibly sensible three-dimensional output, and preferably also includes displaying the extracted information. Additionally or alternatively, the method also includes comparing the visibly sensible three-dimensional output to at least one visibly sensible three-dimensional model.

The present invention successfully addresses the shortcomings of the presently known configurations by providing a system and method for determining presence or absence of one or more thermally distinguishable objects in a living body.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified pictorial illustration of a system for determining presence or absence of a thermally distinguishable object in a living body, operative in accordance with a preferred embodiment of the present invention;

FIGS. 2A-E are simplified pictorial illustrations of five alternative embodiments of one stage of a method in accordance with a preferred embodiment of the present invention;

FIGS. 3A-E are simplified pictorial illustrations of five alternative embodiments of another stage of a method in accordance with a preferred embodiment of the present invention;

FIG. 4 is a flow chart illustration of the computing stage of a method in accordance with a preferred embodiment of the present invention;

FIG. 7 is a simplified pictorial illustration of the final step of the computing stage of a method in accordance with a preferred embodiment of the present invention; and FIG. 8 is a flowchart diagram illustrating a method suitable for determining presence or absence of the thermally distinguishable object, according to various exemplary embodiments of the present invention.

DESCRIPTION OF THE PREFERRED EMBODIMENTS

Figure 2A:
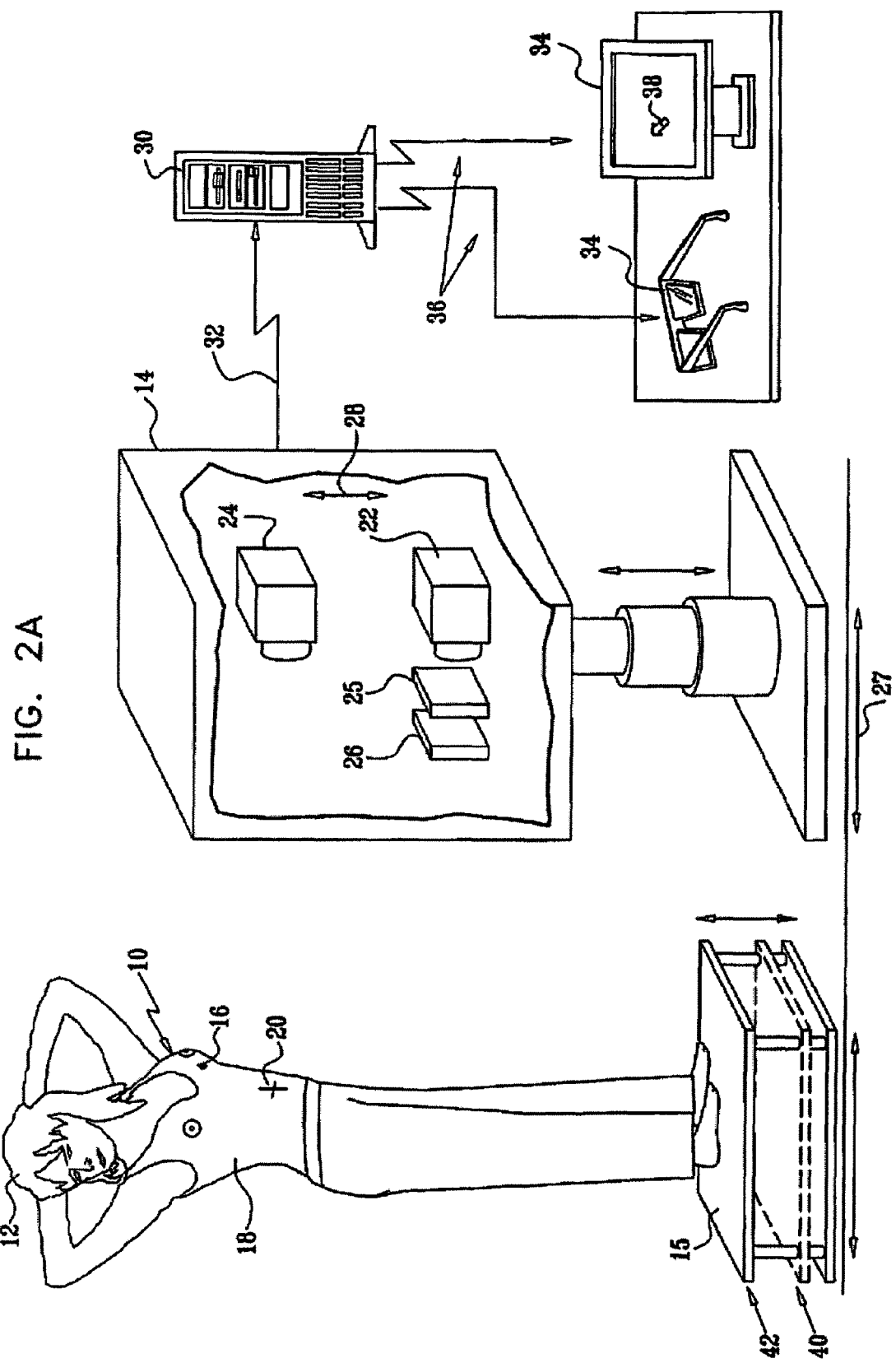

The present embodiments comprise a system and method which can be used for determining presence or absence and optionally the location and/or orientation of a thermally distinguishable object in a living body. The thermally distinguishable object has a temperature which is higher or lower than the temperature of its immediate surrounding. Specifically, the present embodiments can be used to determining presence or absence and optionally the location and/or orientation of thermally distinguishable tissue, such as, but not limited to, inflammation, benign tumor, malignant tumor and the like. The present embodiments are particularly useful for determining the location and/or orientation of superficial, subsurface and deep-seated tumors in a part of the human body, e.g., the breast. Thus, the present embodiments can be used for determining the location and/or orientation of a breast tumor, hence to allow early detection of breast cancer.

The principles and operation of a system and method according to the present embodiments may be better understood with reference to the drawings and accompanying descriptions.

Before explaining at least one embodiment of the invention in detail, it is to be understood that the invention is not limited in its application to the details of construction and the arrangement of the components set forth in the following description, or illustrated in the drawings. The invention is capable of other embodiments or of being practiced or carried out in various ways. Also, it is to be understood that the phraseology and terminology employed herein is for the purpose of description and should not be regarded as limiting.

In its simplest configuration, the system of the present embodiments comprises a combined image generator, which is preferably configured for combining non-thermographic three-dimensional (3D) data of a 3D tissue region in the living body with thermographic two-dimensional (2D) data of the tissue region so as to generate 3D temperature data associated with the tissue region. The 2D data can describe, for example, the surface of the tissue region. Optionally and preferably the system further comprises non-thermographic image data acquisition functionality configured for acquiring the non-thermographic 3D data. Additionally, the system can further comprise thermographic image data acquisition functionality configured for acquiring the thermographic 2D data. In various exemplary embodiments of the invention the image data acquisition functionality or functionalities are contained in housing. Preferably, both the non-thermographic and the thermographic image data acquisition functionalities are contained in the same housing.

The combined image generator preferably comprises a computing device which calculates the location of the thermally distinguishable object in the 3D tissue region, based on the 3D temperature data. In various exemplary embodiments of the invention the computing device calculates orientation of the object. Such calculations can be achieved, for example, by identifying thermally isolated temperature data (e.g., by thresholding) and using the 3D temperature data for associating these thermally isolated data with a spatial location and/or orientation in the living body. The computing device of the present embodiments preferably generates the 3D temperature data by computing a non-thermographic 3D model of the tissue region and 3D spatial data associated with the model. The computing device receives the 2D thermographic data and embeds the 2D data into the 3D model. The computing device uses the 3D for generating spatial data pertaining to the location and/or orientation of the thermally distinguishable object within the living body.

The 2D thermographic data can be in the form of temperature data associated with 2D spatial information. For example, the 2D thermographic data can be in the form of a plurality of temperature values, each being associated with a different 2D coordinate (e.g., X-Y Cartesian coordinate). Typically, but not obligatorily, such 2D thermographic data can be visually presented as a thermal image comprising a plurality of pixel data points, where each pixel provides temperature information which is displayed using a color, grayscale or symbolic code. The 2D thermographic data can also include more than one dataset. For example, the 2D thermographic data can include two or more thermal images obtained simultaneously or sequentially from different perspective viewpoints with respect to the surface of the tissue region.

Referring now to the drawings, the method of the present embodiments is illustrated in the flowchart diagram of FIG. 8.

It is to be understood that, unless otherwise defined, the method steps described hereinbelow can be executed either contemporaneously or sequentially in many combinations or orders of execution. Specifically, the ordering of the flowchart diagrams is not to be considered as limiting. For example, two or more method steps, appearing in the following description or in the flowchart diagrams in a particular order, can be executed in a different order (e.g., a reverse order) or substantially contemporaneously. Additionally, several method steps described below are optional and may not be executed.

The method basically comprises a stage 83 in which the non-thermographic 3D data of the tissue region is combined with the thermographic 2D data of the region so as to generate the 3D temperature data. In various exemplary embodiments of the invention the method also uses the 3D temperature data for determining the location and/or orientation of the thermally distinguishable object (stage 84) as further detailed hereinabove. The method can further comprise one or more data acquisition steps (stages 81 and 82) in which non-thermographic (stage 81) and/or thermographic data (stage 82) are acquired. For example, two or more non-thermographic 2D datasets can be acquired, simultaneously or sequentially. In this embodiments the non-thermographic 2D datasets are combined to provide non-thermographic 3D data as known in the art (see, e.g, U.S. Pat. Nos. 6,201,541, 6,801,257 and 6,701,081).

When more the one thermographic 2D dataset is acquired, each such thermographic dataset is combined with the non-thermographic 3D data as further detailed hereinabove. Alternatively, the thermographic 2D datasets can be combined to form a thermographic three-dimensional model, as further detailed hereinunder.

According to a preferred embodiment of the present invention the method continues to step 85 in which a visibly sensible 3D output is displayed. Optionally and preferably the method continues to step 86 in which the 3D temperature data is compared to a 3D model.

The method ends at step 87.

Reference is now made to FIG. 1 which is a schematic illustration of the system in accordance with preferred embodiments of the present invention. As shown in FIG. 1, a body part 10 of a person 12 is located in front of an imaging device 14. The person 12, may be standing, sitting or in any other suitable position relative to imaging device 14. Person 12 may initially be positioned or later be repositioned relative to imaging device 14 by positioning device 15, which typically comprises a platform moving on a rail, by force of an engine, or by any other suitable force. Additionally, a tumor 16 may exist in body part 10 of person 12. Typically, body part 10 comprises a breast, and tumor 16 comprises a breast tumor such as a cancerous tumor.

In accordance with a preferred embodiment of the present invention, person 12 may be wearing a clothing garment 18, such as a shirt. Preferably, clothing garment 18 may be non-penetrable or partially penetrable to visible wavelengths such as 400-700 nanometers, and may be penetrable to wavelengths that are longer than visible wavelengths, such as IR wavelengths. Additionally, a reference mark 20 may be located close to person 12, preferably directly on the body of person 12 and in close proximity to body part 10. Optionally and preferably, reference mark 20 is directly attached to body part 10. Reference mark 20 may typically comprise a piece of material, a mark drawn on person 12 or any other suitable mark, as described herein below.

Imaging device 14 typically comprises at least one non-thermographic imaging system 22 that can sense at least visible wavelengths and at least one thermographic imaging system 24 which is sensitive to infra-red (IR) wavelengths, typically in the range of as 3-5 micrometer and/or 8-12 micrometer. Typically imaging systems 22 and 24 are capable of sensing reference mark 20 described hereinabove.

Optionally, a polarizer 25 may be placed in front of non-thermographic imaging system 22. As a further alternative, a color filter 26, which may block at least a portion of the visible wavelengths, may be placed in front of non-thermographic imaging system 22.

Typically, at least one non-thermographic imaging system 22 may comprise a black-and-white or color stills camera, or a digital camera such as CCD or CMOS. Additionally, at least one non-thermographic imaging system 22 may comprise a plurality of imaging elements, each of which may be a three-dimensional imaging element.

Optionally, imaging device 14 may be repositioned relative to person 12 by positioning device 27. As a further alternative, each of imaging systems 22 and 24 may also be repositioned relative to person 12 by at least one positioning device 28. Positioning device 27 may comprise an engine, a lever or any other suitable force, and may also comprise a rail for moving imaging device 14 thereon. Preferably, repositioning device 28 may be similarly structured.

Data acquired by non-thermographic imaging system 22 and thermographic imaging system 24 is output to a computing device 30 via a communications network 32, and is typically analyzed and processed by an algorithm running on the computing device. The resulting data may be displayed on at least one display device 34, which is preferably connected to computing device 30 via a communications network 36. Computing device 30 typically comprises a PC, a PDA or any other suitable computing device. Communications networks 32 and 36 typically comprise a physical communications network such as an internet or intranet, or may alternatively comprise a wireless network such as a cellular network, IR communication network, a radio frequency (RF) communications network, a blue-tooth (BT) communications network or any other suitable communications network.

In accordance with a preferred embodiment of the present invention display 34 typically comprises a screen, such as an LCD screen, a CRT screen or a plasma screen. As a further alternative display 34 may comprise at least one visualizing device comprising two LCDs or two CRTs, located in front of a user's eyes and packaged in a structure similar to that of eye-glasses. Preferably, display 34 also displays a pointer 38, which is typically movable along the X, Y and Z axes of the displayed model and may be used to point to different locations or elements in the displayed data.

Reference is now made to FIGS. 2A-4, which illustrate various stages in method of 3D non-thermographic and thermographic imaging of a portion of a human body, in accordance with a preferred embodiment of the present invention.

As seen in FIG. 2A, person 12 comprising body part 10 is located on a positioning device 15 in front of an imaging device 14, in a first position 40 relative to the imaging device. First image data of body part 10 is acquired by at least one non-thermographic imaging system 22, optionally through polarizer 25 or as an alternative option through color filter 26. Additionally, at least second image data of body part 10 is acquired by at least one non-thermographic imaging system 22, such that body part 10 is positioned in at least a second position 42 relative to imaging device 14.

Figure 2B:
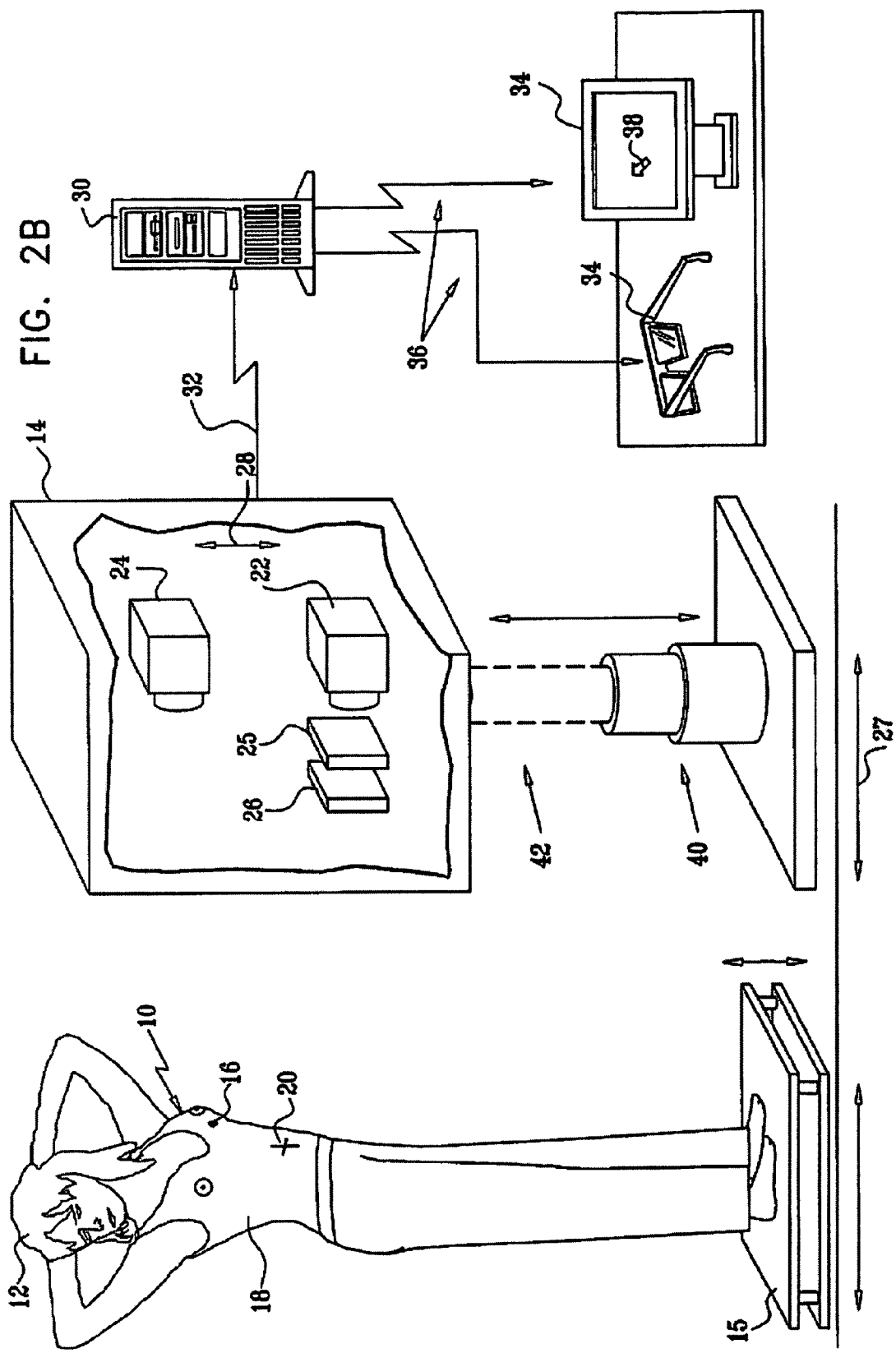
Figure 2C:
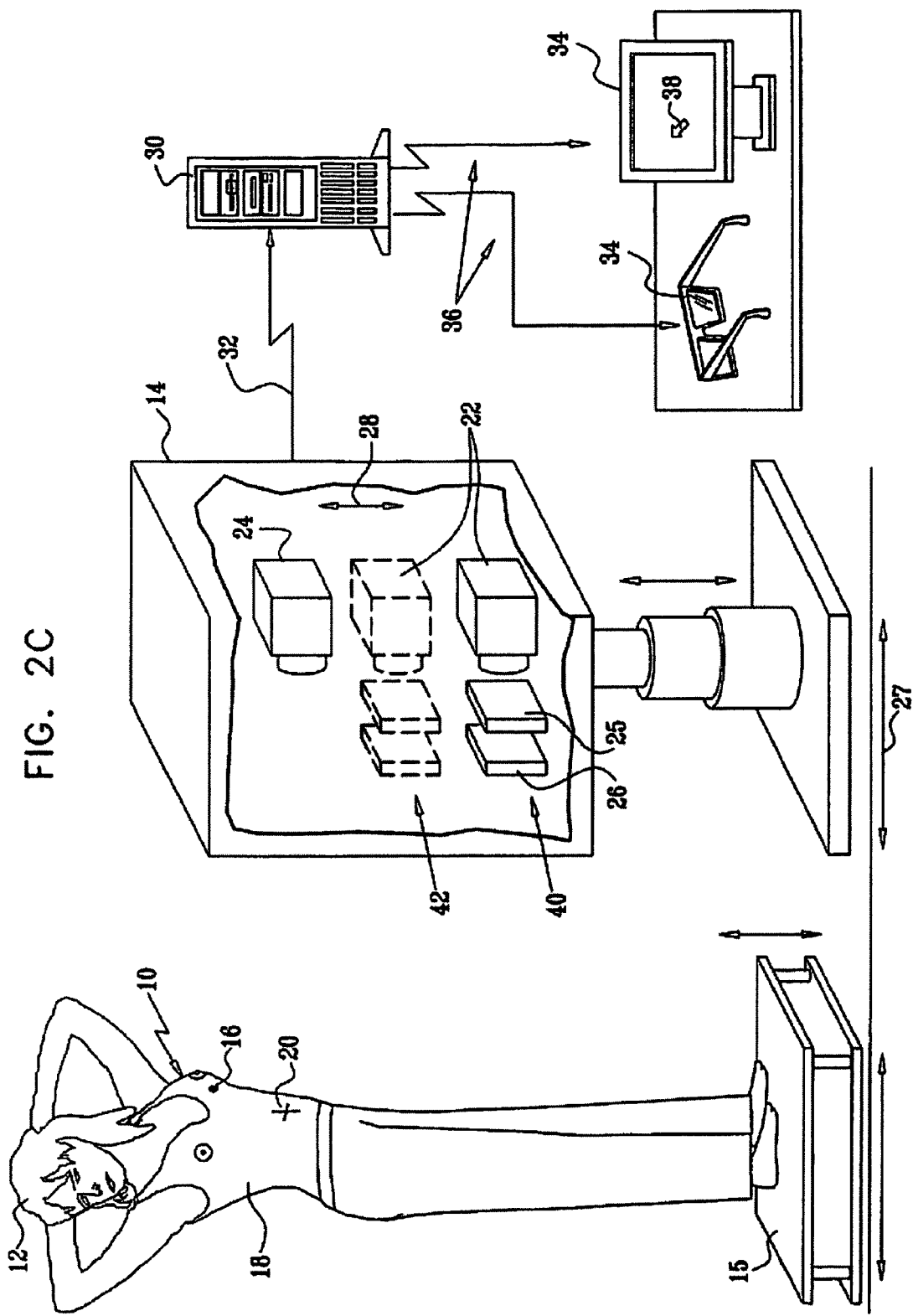
Figure 2E:
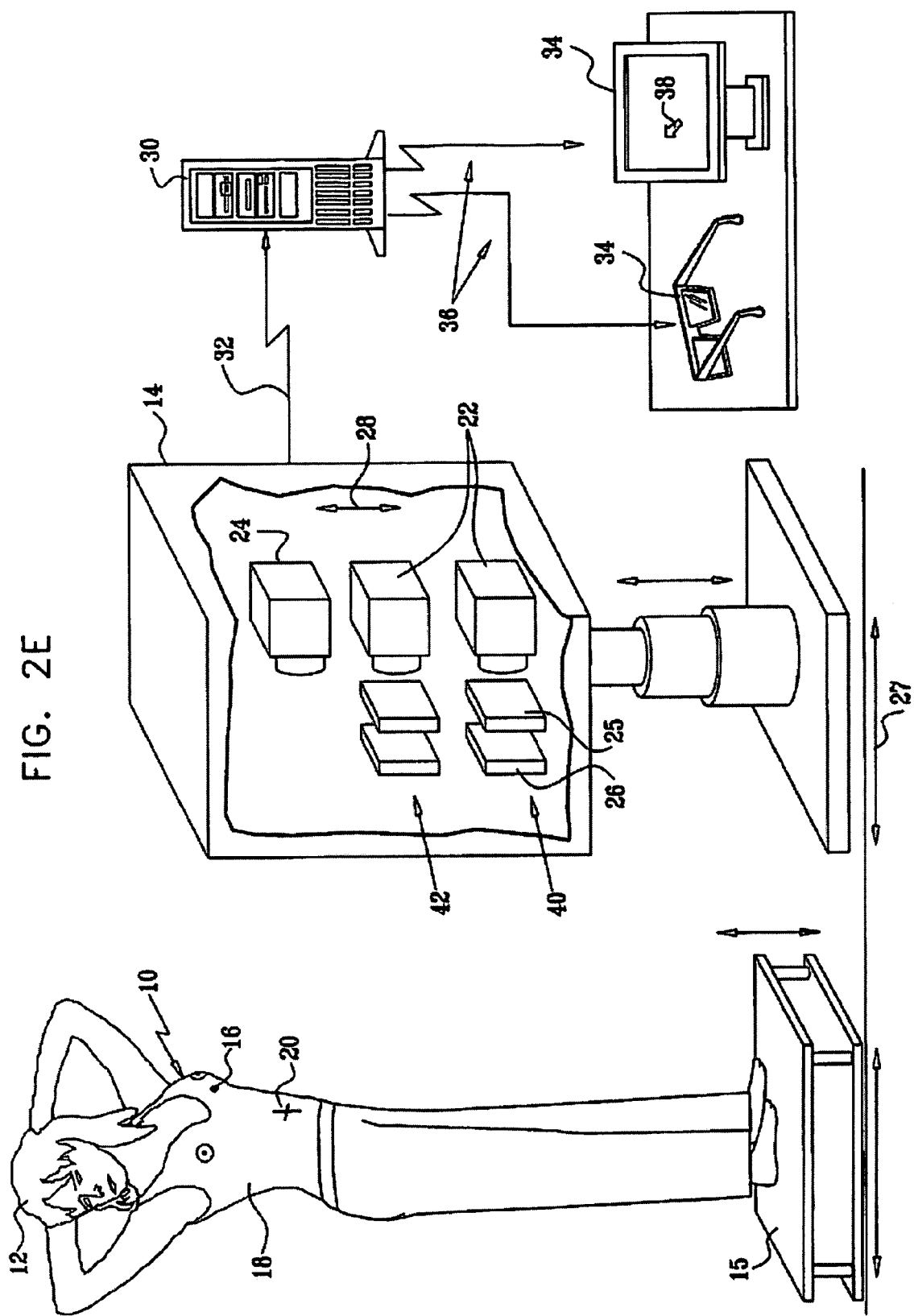

The second relative position 42 may be configured by repositioning person 12 using positioning device 15 as seen in FIG. 2A, by repositioning imaging device 14 using positioning device 27 as seen in FIG. 2B or by repositioning non-thermographic imaging system 22 using positioning device 28 as seen in FIG. 2C. As a further alternative, the second relative position 42 may be configured by using two separate imaging devices 14 as seen in FIG. 2D or two separate non-thermographic imaging systems 22 as seen in FIG. 2E.

In a further stage of the method in accordance with a preferred embodiment of the present invention, person 12 comprising body part 10 is located on a positioning device 15 in front of an imaging device 14, in a first position 44 relative to the imaging device. First thermographic image data of body part 10 is acquired by at least one thermographic imaging system 24. Additionally, at least second thermographic image data of body part 10 is acquired by at least one thermographic imaging system 24, such that body part 10 is positioned in at least a second position 42 relative to imaging device 14.

Figure 3B:
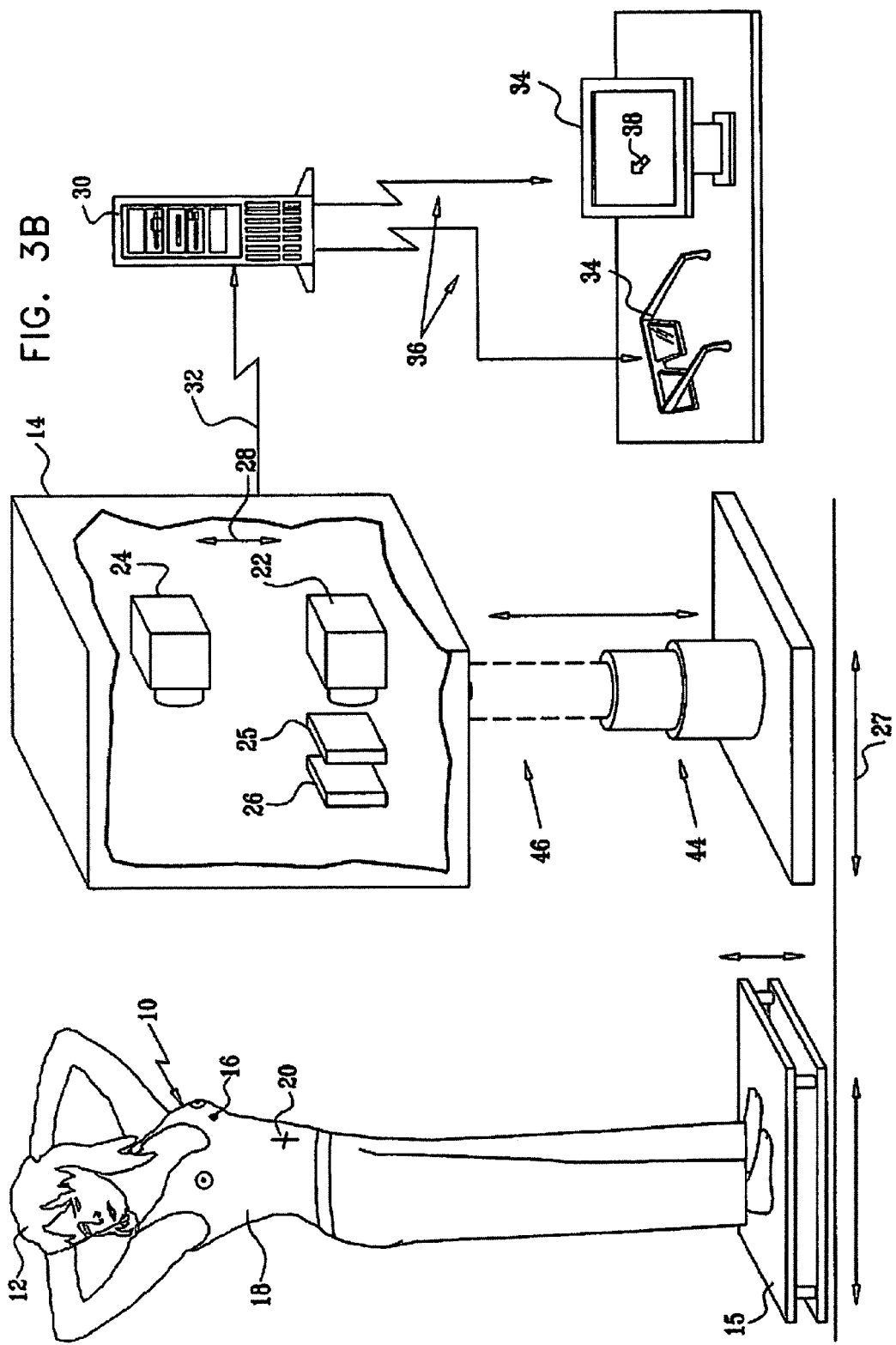
Figure 3C:
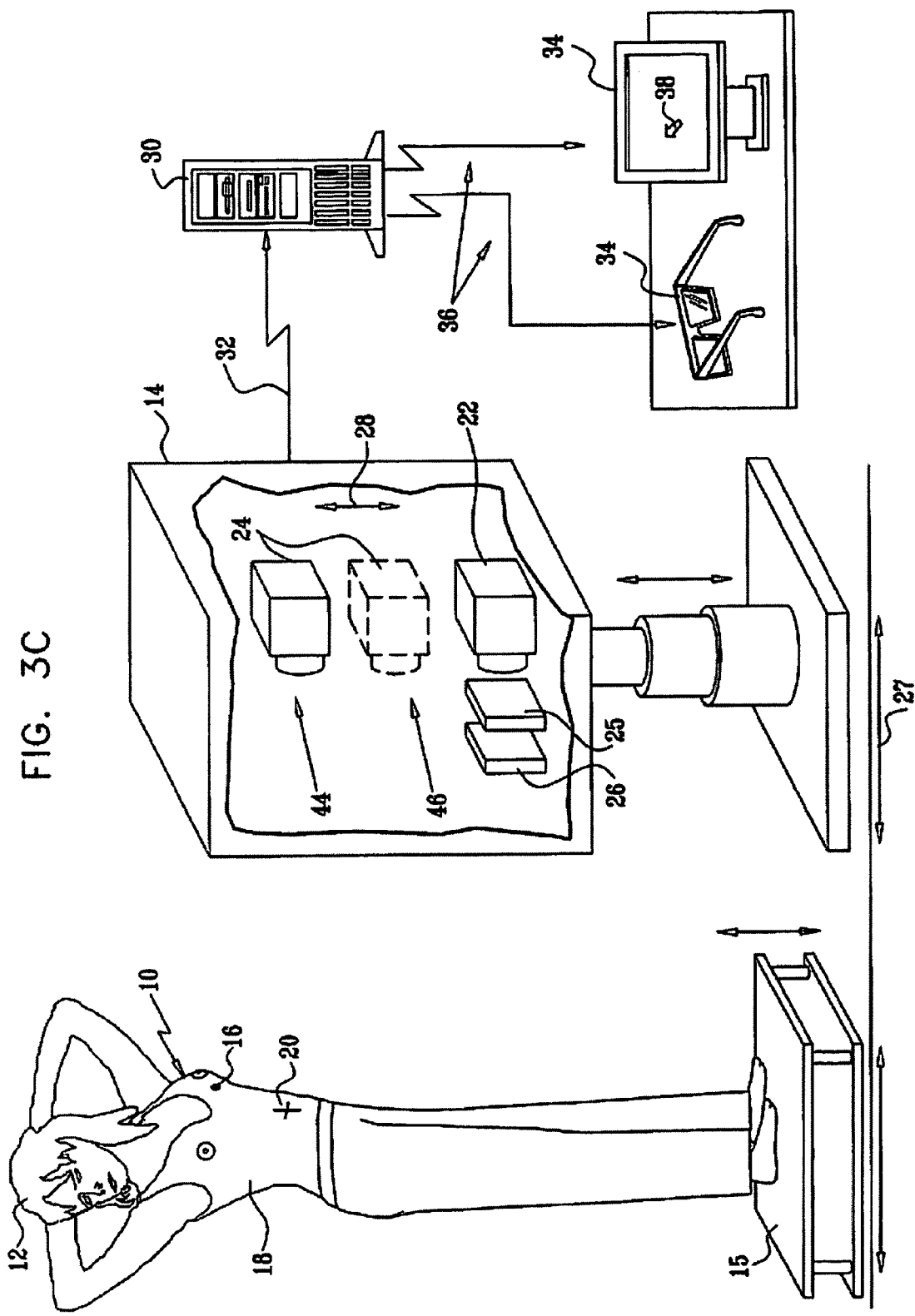
Figure 3D:
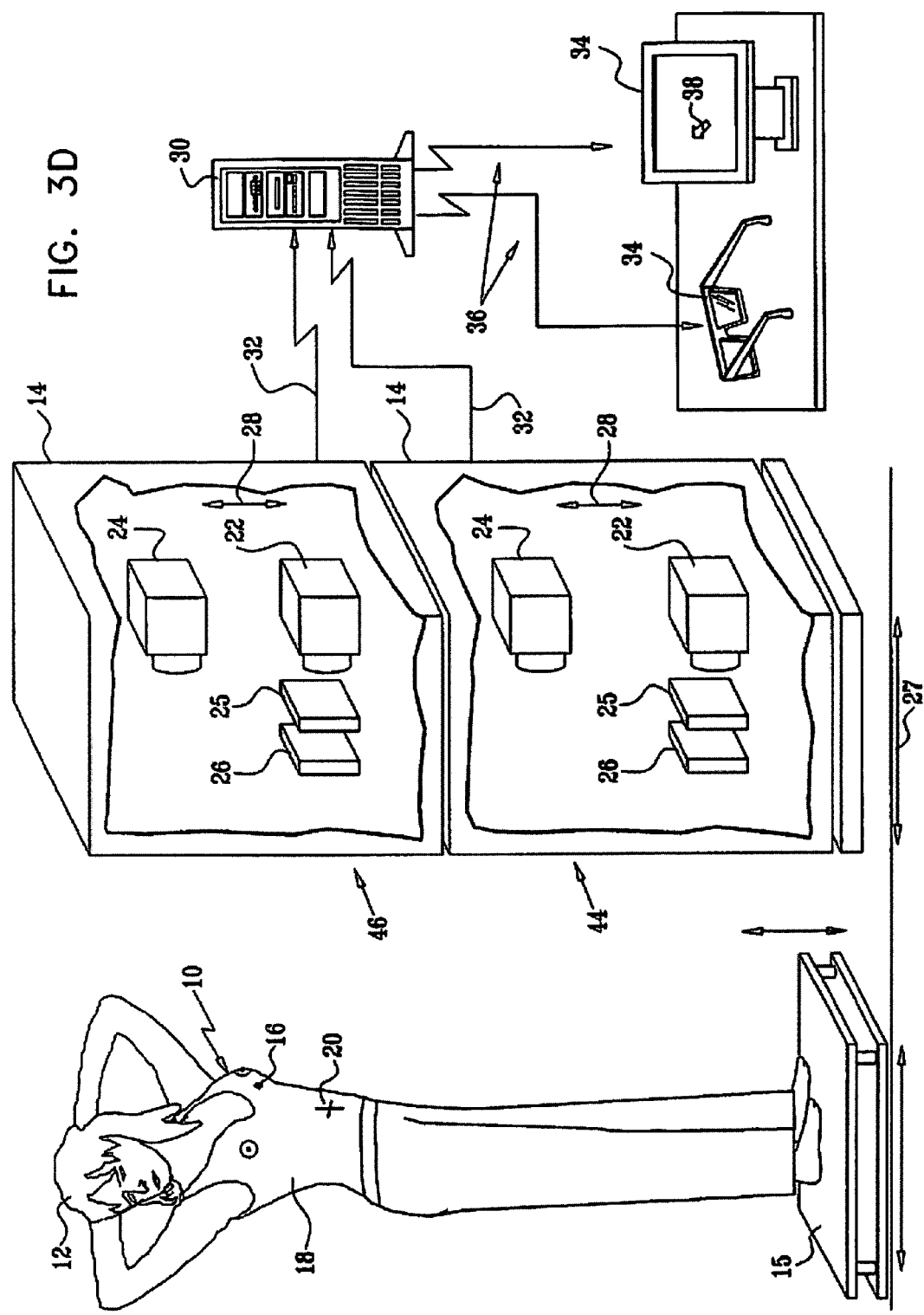
Figure 3E:
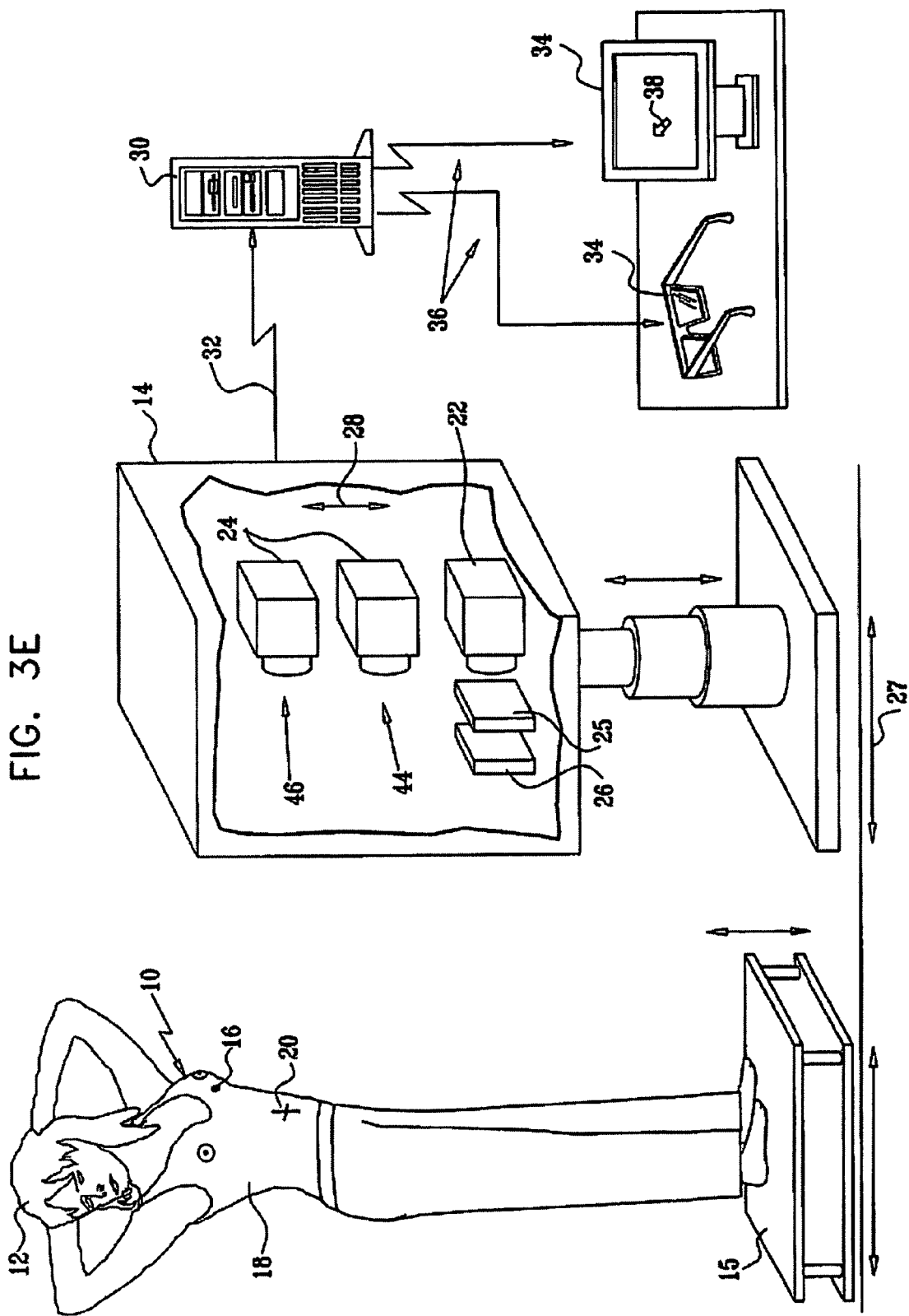

The second relative position 46 may be configured by repositioning person 12 using positioning device 15 as seen in FIG. 3A, by repositioning imaging device 14 using positioning device 27 as seen in FIG. 3B, or by repositioning thermographic imaging system 24 using positioning device 28 as seen in FIG. 3C. As a further alternative, the second relative position 46 may be configured by using two separate imaging devices 14 as seen in FIG. 3D or two separate thermographic imaging systems 24 as seen in FIG. 3E.

It will be appreciated that the non-thermographic image data acquisition described in FIGS. 2A-2E may be performed before, after or concurrently with the thermographic image data acquisition described in FIGS. 3A-3E.

Image data of body part 10 may be acquired by thermographic imaging system 24, by separately imaging a plurality of narrow strips of the complete image of body part 10. Alternatively, the complete image of body part 10 is acquired by thermographic imaging system, and the image is sampled in a plurality of narrow strips or otherwise shaped portions for processing. As a further alternative, the imaging of body part 10 may be performed using different exposure times.

The thermographic and non-thermographic image data obtained from imaging device 14 is analyzed and processed by computing device 30 as illustrated in FIG. 4.

Figure 5:
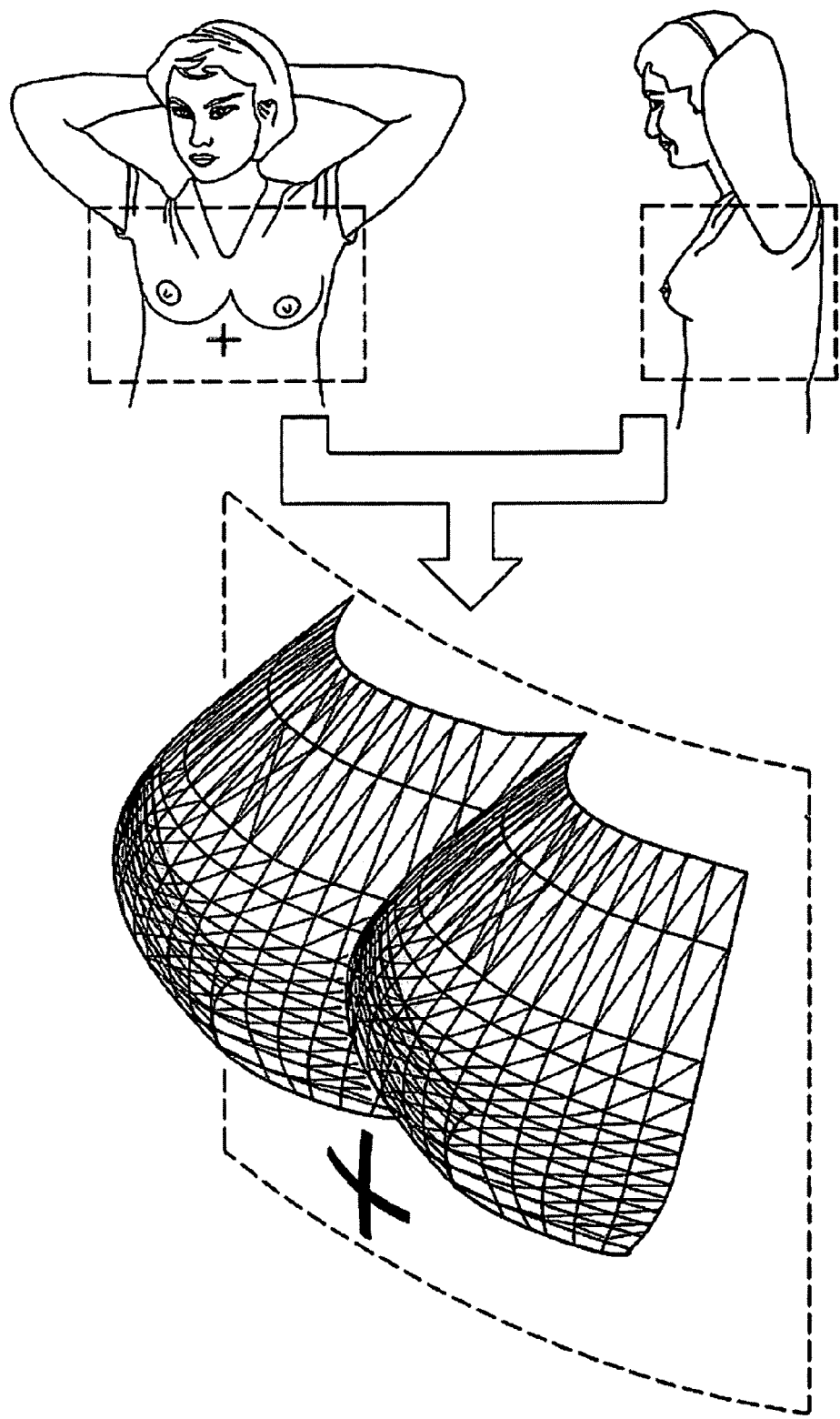
FIG. 5 is a simplified pictorial illustration of an initial step of the computing stage of a method in accordance with a preferred embodiment of the present invention.

In stage 50, image data acquired from non-thermographic imaging system 22 is processed by computing device 30 to build a non-thermographic three-dimensional model of body part 10 of person 12, using algorithms and methods that are well known in the art, such as the method described in U.S. Pat. No. 6,442,419 which is hereby incorporated by reference as if fully set forth herein. The non-thermographic three-dimensional model, preferably includes spatial information, typically the X, Y and Z coordinates of the body part 10, as well as the location of reference marker 20. Additionally, the non-thermographic three-dimensional model preferably includes information relating to the color, hue and tissue texture of body part 10. An exemplary non-thermographic three-dimensional model and the process of building such a model are illustrated in FIG. 5.

Figure 6:
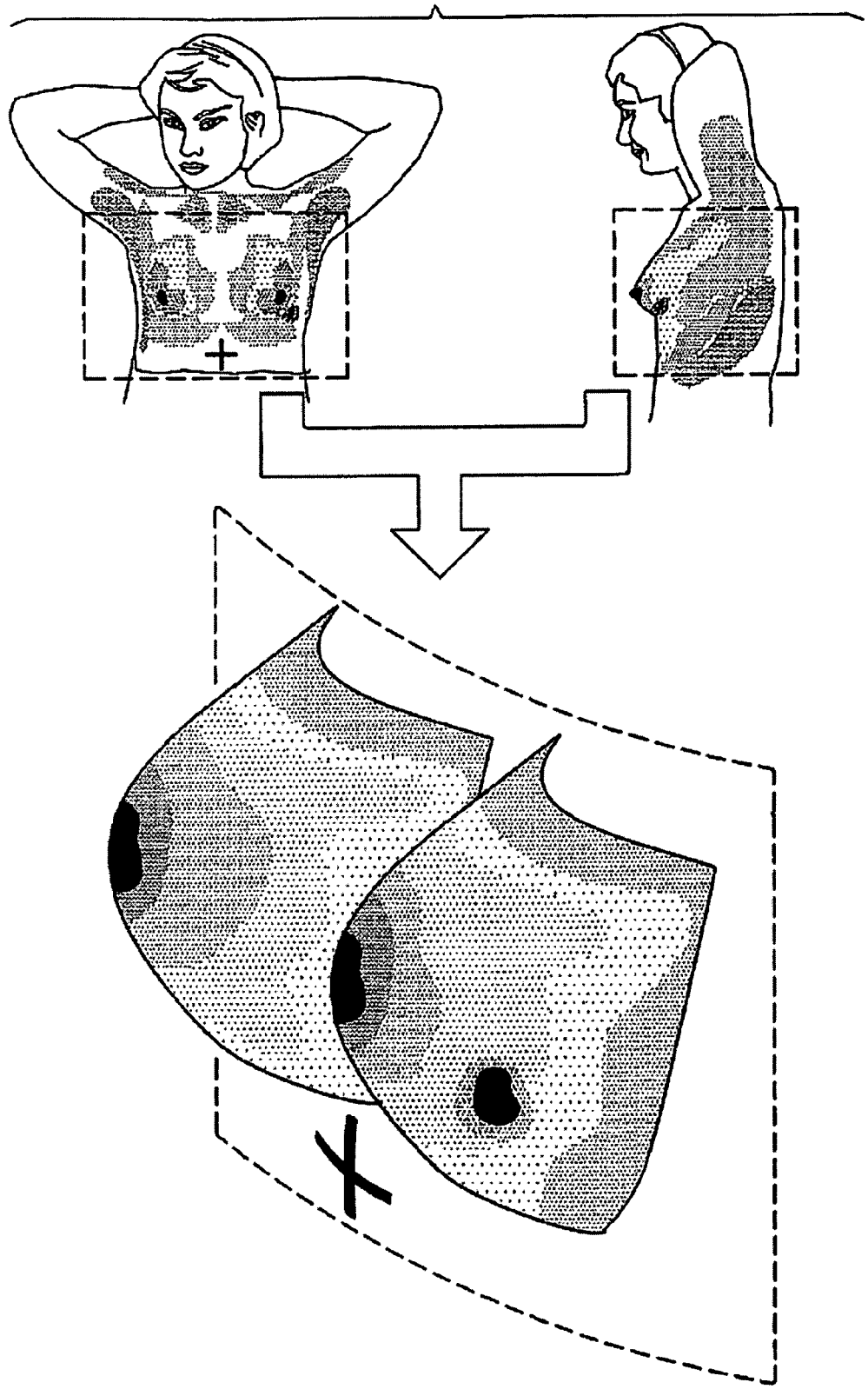
FIG. 6 is a simplified pictorial illustration of another step of the computing stage of a method in accordance with a preferred embodiment of the present invention.

Thermographic image data acquired from thermographic imaging system 24 is processed by computing device 30 in stage 52 to build a thermographic three-dimensional model of body part 10 of person 12, using algorithms and methods that are well known in the art, such as the method described in U.S. Pat. No. 6,442,419 which is hereby incorporated by reference as if fully set forth herein. The thermographic three-dimensional model preferably includes spatial temperature information, typically the X, Y and Z coordinates of the temperature of body part 10 and of reference marker 20. An exemplary thermographic three-dimensional model and the process of building such a model are illustrated in FIG. 6.

It is appreciated that the thermographic three-dimensional model may be built before, after or concurrently with the non-thermographic three-dimensional model.

The three-dimensional models built in stages 50 and 52 as described hereinabove are combined into a single three-dimensional model in stage 54. Correct positioning of the two models in the combined three-dimensional model may be achieved by accurately positioning reference marker 20 in the two models, by comparing X, Y and Z coordinates or using any other suitable method. An exemplary combined three-dimensional model as built in stage 54 is illustrated in FIG. 7.

In stage 56, computing device 30 extracts information included in the combined three-dimensional model, such as information regarding temperature, temperature changes in a certain point and a comparison of temperatures in different points in body part 10. Additionally, computing device 30 may extract, compute and display a comparison of size or temperature between body part 10 and another body part of person 12, such as the two breasts of person 12.

In an additional or alternative stage 58, the computing device 30 may compare and display differences between a plurality of three-dimensional models of the same body part 10 of a person 12, the plurality of models being based on data acquired at a plurality of different time points. Typically, the information compared, computed and displayed includes information about temperature, dimensions such as length, width, height and depth, shape, volume, color, hue and tissue texture. The information may be displayed graphically or textually, and may be described as a change in percentage or in absolute value.

As shown in stage 60, the output of any of stages 54, 56 and 58 is displayed on display 34. Pointer 38 is also displayed, and may be used to point to sections or elements of the displayed model, along any of the X, Y and Z coordinates. Optionally and preferably, an algorithm is provided to facilitate the display of sectional views of the three-dimensional model or of specific tissue layers of the modeled body part 10.

It will be appreciated by persons skilled in the art that the present invention is not limited to what has been particularly shown and described hereinabove. Rather the scope of the present invention includes both combinations and subcombinations of the various features described hereinabove as well as modifications and variations thereof as would occur to a person of skill in the art upon reading the foregoing specification and which are not in the prior art.

It is expected that during the life of this patent many relevant data acquisition techniques will be developed and the scopes of the terms thermographic data and non-thermographic data are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for determining presence or absence of a thermally distinguishable object in a living body, the system comprising: a combined image generator configured for combining non-thermographic three-dimensional data of a three-dimensional tissue region in the living body with thermographic two-dimensional data of said tissue region so as to generate three-dimensional temperature data associated with said three-dimensional tissue region.

2. The system of claim 1, further comprising non-thermographic image data acquisition functionality configured for acquiring said non-thermographic three-dimensional data.

3. The system of claim 2, further comprising thermographic image data acquisition functionality configured for acquiring said thermographic two-dimensional data.

4. The system of claim 2, wherein said non-thermographic image data acquisition functionality comprises a stills camera or a digital camera.

5. The system of claim 2, wherein said non-thermographic image data acquisition functionality comprises a plurality of cameras configured and positioned for acquiring a plurality of non-thermographic two-dimensional datasets from a plurality of perspective viewpoints with respect to the surface of said three-dimensional tissue region.

6. The system of claim 5, wherein said non-thermographic image data acquisition functionality comprises a combiner configured for combining said plurality of non-thermographic two-dimensional datasets so as to form said non-thermographic three-dimensional data.

7. The system of claim 1, further comprising thermographic image data acquisition functionality configured for acquiring said thermographic two-dimensional data.

8. The system of claim 3, further comprising a housing containing said non-thermographic image data acquisition functionality and said thermographic image data acquisition functionality.

9. The system of claim 7, wherein said thermographic image data acquisition functionality comprises a plurality of infrared cameras configured and positioned for acquiring a plurality of thermographic two-dimensional datasets from a plurality of perspective viewpoints with respect to the surface of said three-dimensional tissue region.

10. The system of claim 9, wherein said combined image generator is configured for combining said non-thermographic three-dimensional data with each thermographic two-dimensional dataset.

11. The system of claim 7, further comprising a positioning device operative to reposition said non-thermographic image data acquisition functionality or said thermographic image data acquisition functionality.

12. The system of claim 3, further comprising a communications network configured for establishing said communication between at least two of said non-thermographic image data acquisition functionality, said thermographic image data acquisition functionality and said combined image generator.

13. The system of claim 1, further comprising a positioning device operative to reposition said housing.

14. The system of claim 1, wherein said combined image generator comprises a computing device configured for calculating the location and/or orientation of the thermally distinguishable object in the three-dimensional tissue region, based on said three-dimensional temperature data.

15. The system of claim 14, further comprising a display, wherein said computing device is in communication with said display and is configured for transmitting a visibly sensible three-dimensional output indicating said location and/or orientation to said display.

16. The system of claim 15, further comprising a communication network configured for establishing said communication between said computing device and said display.

17. The system of claim 15, wherein said display comprises two LCDs or two CRTs packaged together in an eye-glasses structure.

18. The system of claim 15, wherein said display is operative to display a pointer.

19. The system of claim 14, wherein said computing device is configured for computing a non-thermographic three-dimensional model, and computing spatial data of said non-thermographic three-dimensional model so as to generate spatial data pertaining to the location and/or orientation of the thermally distinguishable object within the living body.

20. The system of claim 19, wherein said computing device is configured for computing spatial temperature data of said non-thermographic three-dimensional model.

21. The system of claim 1, further comprising a comparing functionality configured for comparing said three-dimensional temperature data to at least one three-dimensional model.

22. The system of claim 1, wherein said non-thermographic three-dimensional data comprise a combination of a plurality of two-dimensional images.

23. The system of claim 1, wherein said thermally distinguishable object comprises a tumor.

24. The system of claim 23, wherein said tumor comprises a cancerous tumor.

25. The system of claim 1, further comprising a positioning device operative to reposition the living body.

26. A method of determining presence or absence of a thermally distinguishable object in a living body, the method comprising: combining non-thermographic three-dimensional data of a three-dimensional tissue region in the living body with thermographic two-dimensional data of said tissue region so as to generate three-dimensional temperature data associated with said three-dimensional tissue region, thereby determining the presence or absence of the thermally distinguishable object.

27. The method of claim 26, further comprising using said three-dimensional temperature data for determining the location and/or orientation of the thermally distinguishable object in the three-dimensional tissue region.

28. The method of claim 27, further comprising providing a visibly sensible three-dimensional output indicating said location and/or orientation.

29. The method of claim 26, further comprising comparing said three-dimensional temperature data to at least one three-dimensional model.

30. The method of claim 26, wherein said non-thermographic three-dimensional data are obtained by combining a plurality of two-dimensional images.

31. The method of claim 26, wherein said non-thermographic three-dimensional data comprise a three-dimensional image acquired using a visible light camera.

32. The method of claim 26, further comprising acquiring said non-thermographic three-dimensional data using at least one non-thermographic image data acquisition functionality.

33. The method of claim 32, wherein said acquiring said non-thermographic three-dimensional data comprises a plurality of sequential data acquisition steps, and the method further comprises repositioning at least one of said data acquisition functionality and the living body between successive data acquisition steps.

34. The method of claim 33, wherein said plurality of sequential data acquisition steps comprises a first two-dimensional data acquisition step performed at a first perspective view and a second two-dimensional data acquisition step performed at a second perspective view, and the method further comprises combining two-dimensional data from said first step and said second step so as to form said non-thermographic three-dimensional data.

35. The method of claim 32, wherein said acquiring said non-thermographic three-dimensional data comprises simultaneously acquiring non-thermographic two-dimensional datasets from a plurality of perspective viewpoints with respect to the surface of said three-dimensional tissue region, and the method further comprises combining said plurality of non-thermographic two-dimensional datasets so as to form said non-thermographic three-dimensional data.

36. The method of claim 26, further comprising acquiring said thermographic two-dimensional data, using at least one thermographic image data acquisition functionality.

37. The method of claim 36, wherein said acquiring said thermographic two-dimensional data comprises a plurality of sequential data acquisition steps, and the method further comprises repositioning at least one of said data acquisition functionality and the living body between successive data acquisition steps.

38. The method of claim 36, wherein said acquiring said thermographic two-dimensional data comprises simultaneously acquiring thermographic two-dimensional datasets from a plurality of perspective viewpoints with respect to the surface of said three-dimensional tissue region, and the method further comprises combining each thermographic two-dimensional dataset with said non-thermographic three-dimensional data.

39. The method of claim 37, wherein said combining is performed such that data acquired at each thermographic two-dimensional data acquisition step is combined with said non-thermographic three-dimensional data.

40. The method of claim 26, wherein said combining comprises computing a non-thermographic three-dimensional model, and computing spatial data of said non-thermographic three-dimensional model so as to generate spatial data pertaining to the location and/or orientation of the thermally distinguishable object within the living body.

41. The method of claim 40, wherein said combining comprises computing spatial temperature data of said non-thermographic three-dimensional model.

* * * * *